United States Patent [19]

Gezari et al.

[11] 4,285,340
[45] Aug. 25, 1981

[54] APPARATUS FOR CONTROLLING THE PRESSURE IN A TRACHEAL CUFF

[76] Inventors: Walter A. Gezari, R.F.D. #2, Box 76; James Crittenden, 133 Parker Hill Rd., both of Killingworth, Conn. 06417

[21] Appl. No.: 21,072

[22] Filed: Mar. 16, 1979

[51] Int. Cl.³ .......................................... A61M 16/00
[52] U.S. Cl. ........................ 128/205.24; 128/207.15; 137/102
[58] Field of Search ............ 128/351, 349 B, 349 BV, 128/145.6, 145.8, 208, 204.24, 204.25, 205.24, 207.14, 207.15, 207.16; 137/102

[56] References Cited

U.S. PATENT DOCUMENTS

| 3,265,061 | 8/1966 | Gage, Jr. | 128/145.8 |
| 3,504,676 | 4/1970 | Lomholt | 128/349 BV |
| 3,529,596 | 9/1970 | Garner | 128/351 X |
| 4,155,357 | 5/1979 | Dahl | 128/145.8 |

Primary Examiner—Henry J. Recla
Attorney, Agent, or Firm—Fishman and Van Kirk

[57] ABSTRACT

An apparatus for controlling the pressure in a tracheal cuff used with a tracheal tube to seal the walls of the trachea with respect to the tube, the cuffed tracheal tube being of the type used with an automatic respirator which cycles between an inhalation mode and an exhalation mode.

24 Claims, 5 Drawing Figures

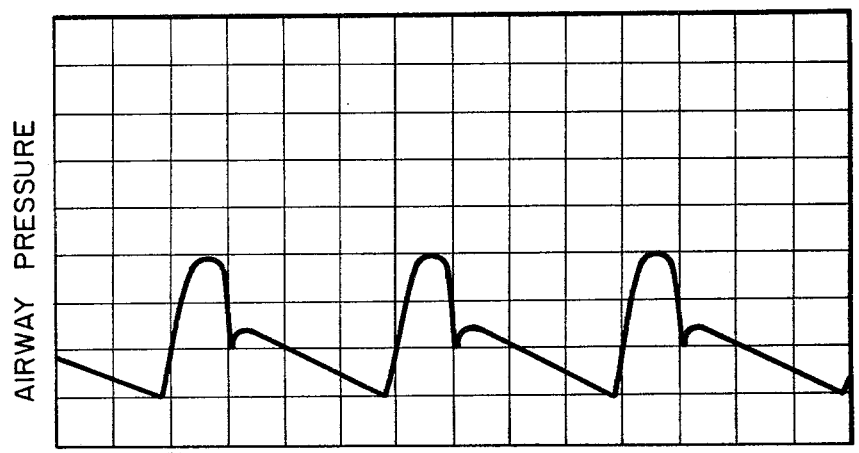
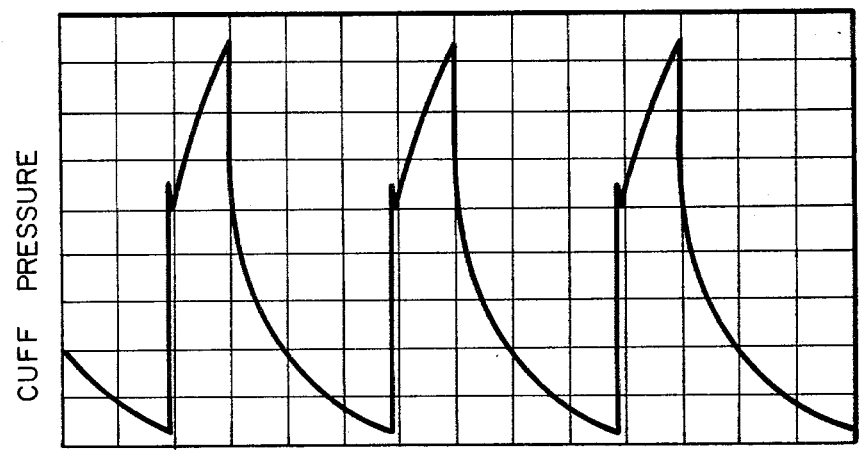
FIG. 3
FIG. 4

APPARATUS FOR CONTROLLING THE PRESSURE IN A TRACHEAL CUFF

BACKGROUND OF THE INVENTION (1) Field of the Invention

This invention relates to respiratory apparatus and more particularly to apparatus for controlling the pressure in cuffs of tracheal tubes.

(2) Description of the Prior Art

During controlled ventilation in patients on automatic respirators, a tracheal tube is inserted into the trachea. During the inhalation mode of the respirator, it is necessary to seal the tube with respect to the trachea so that gas passing through the tracheal tube is forced into the lungs of the patient.

To seal the tube with respect to the trachea, the tracheal tube is provided with a pressure cuff which presses against the trachea once the tube is positioned within the trachea. Patients may often require respiratory support for several days or weeks. During lengthy respirator support, it is not unusual for the inner walls of the trachea to become ischemic. The contact between the cuff and the trachea may lead to ulceration, fistulization into an adjacent material branch, and possible stenosis of the tissues lining the inner wall of the trachea. The damage of the inner wall of the trachea is believed to be, at least in part, due to the fact that the pressure of the cuff when fully inflated is sufficient to reduce or terminate blood circulation to the cells in the region of the inner wall of the trachea.

It is well known that the cuff can be inflated during the inhalation mode of the respirator and deflated during the exhalation mode of the respirator. During the exhalation mode, the air in the cuff can be released to deflate the cuff and allow blood to circulate to the cells lining the inner wall of the trachea.

U.S. Pat. No. 3,481,339 discloses an endotracheal tube including a cuff which is said to inflate during the inhalation mode and deflate during the exhalation mode. As disclosed in that patent, the cuff surrounding the endotracheal tube is divided into an external subchamber and an internal subchamber; the internal subchamber being in fluid communication with the interior of the endotracheal tube. During the inhalation mode of the respirator, air or other appropriate gas is forced through the tube and is said to inflate the internal subchamber and press the cuff against the trachea. One drawback with the cuff disclosed in Pat. No. 3,481,339 is that the pressure in the cuff during the inhalation mode can not be controlled and is approximately the same or only slightly greater than the pressure in the trachea. Likewise, the pressure in the cuff during the exhalation mode of the respirator can not be controlled. Another obvious disadvantage of the type of cuff proposed in Pat. No. 3,481,339 is that it is quite difficult to manufacture.

U.S. Pat. No. 3,529,596 discloses an automatic volume limited intermittent cuff inflator-deflator. In the device disclosed in Pat. No. 3,529,596, a pneumatic cylinder with a piston operated by a control line from the respirator inflates and deflates the tracheal cuff in response to the cycle of the respirator. One end of the cylinder is connected via a line to the tracheal cuff. As the piston moves back and forth, the cuff is inflated and deflated. One drawback with the device disclosed in Pat. No. 3,529,596 is that the inflation and deflation of the cuff appears to be relatively slow in response to the cycling of the respirator. Another drawback is that the cuff is inflated to a preset VOLUME, which can cause drastic increases in PRESSURE to result from changes of position, coughing, or other physiological variables which affect tracheal diameter.

U.S. Pat. No. 4,020,849 discloses an apparatus for inflation of cuffs for tracheal tubes. That patent discloses a connector member which connects a tracheal tube to the source of breathing air, the connector member incorporating an auxiliary passage having an entrance device for inflating the cuff with the breathing air. The entrance device responds to raised pressure in the connector to admit the breathing air for filling the cuff and responds to a decrease in pressure to close the auxiliary passage at a desired level for retaining sealing pressure in the cuff. It should be noted that the maximum pressure to which the cuff can be inflated is approximately the maximum pressure of the air from the respirator.

U.S. Pat. No. 3,931,822 discloses an automatic alternating cuff endotracheal tube inflator. That patent discloses an endotracheal tube including at least two cuffs which are alternately inflated. The cuffs of the device of Patent No. 3,931,822 are inflated and deflated by a complicated mechanism which includes a lever arm, an electrical solenoid, and an air bellows.

It is one object of the present invention to provide an apparatus for controlling the pressure within a tracheal cuff and which may be used with various known tracheal cuffs.

It is another object of the invention to provide an apparatus for controlling the pressure within a tracheal cuff and which can be adapted to a conventional respirator.

It is another object of the present invention to provide an apparatus which has a relatively fast response time, that is, the cuff is pressurized quickly when the respirator cycles to the inhalation mode.

It is a further object of the present invention to provide an apparatus wherein the pressure of the cuff during the inhalation mode of the respirator may be controlled.

It is another object of the present invention to provide an apparatus wherein the pressure in the cuff during the exhalation mode of the respirator can be controlled.

It is another object of the present invention to provide an apparatus for controlling pressure within tracheal cuffs which will respond to signals from a conventional respirator during conditions of sustained Positive End Expiratory Pressure (PEEP) and Intermittent Mandatory Ventilation (IMV).

It is another object of the present invention to provide an apparatus for controlling the pressure within a tracheal cuff which is pressure-limited, not volume-limited.

SUMMARY OF THE INVENTION

The present invention provides an apparatus for controlling the pressure in a tracheal cuff of a tracheal tube. The tracheal tube is of the type which is used with an automatic respirator which cycles between an inhalation mode and an exhalation mode. In the inhalation mode, air or other gas such as air enriched with oxygen or anesthetic is forced through the tracheal tube into the lungs of the patient. In order to force air into the lungs and prevent leakage of the air through the passage between the trachea and the tracheal tube, the passage is sealed with a tracheal cuff. The tracheal cuff should be inflated to a pressure which is sufficient to seal the cuff with respect to the trachea during the inhalation mode of the respirator. During the exhalation mode of the respirator, the leakage through the passage between the trachea and the tube is less critical and the pressure in the tracheal cuff may be reduced to allow blood to flow to the cells lining the inner wall of the trachea, except during PEEP.

The apparatus for controlling the pressure in the cuff comprises a fluid source which provides a fluid such as air or oxygen having a positive pressure. The cuff is connected to a valve, which operates between a cuff-filling mode and a cuff-emptying mode. In the cuff-filling mode, fluid passes from the source to the cuff. In the cuff-emptying mode fluid is prevented from passing from the source to the cuff, and fluid passes from the cuff to a pressure release mechanism which provides for release of the pressure within the cuff to a predetermined limit. The apparatus of the present invention further includes a control mechanism for operating the valve. The control mechanism is responsive to the cycling of the respirator to operate the valve to the cuff-filling position to provide for positive pressurization of the cuff during the inhalation mode of the respirator. The control mechanism also operates the valve to the cuff-emptying mode to provide for release of at least a portion of the pressure in the cuff during the exhalation mode of the respirator.

In order to provide a cuff which pressurizes quickly, that is, a cuff having a relatively short response time, a fluid is presented to the cuff through the valve. This operating fluid is pressurized to a level substantially higher than the pressure to which the cuff is to be pressurized. Connected in the circuit between the valve and the cuff is a pressure relief valve which allows for release of some of the fluid when undesirably high pressures are reached. Thus, when the valve is operated to the cuff-filling mode, the cuff is almost instantaneously pressurized by a burst of pressurized fluid. The relief valve provides for release of exceedingly high pressures. Thus, the cuff responds quickly when the cuff-filling valve is actuated.

During the exhalation mode of the respirator, the valve is moved to the cuff-emptying mode and pressurized fluid is allowed to escape through a pressure release mechanism. The pressure release mechanism provides for release of pressure to a predetermined level. Thus, the pressure release mechanism could provide for positive pressure within the cuff during the exhalation mode, that is, a pressure between atmospheric pressure and the maximum pressure in the cuff. The pressure release mechanism could also simply be a vent to atmosphere. Furthermore, the pressure release mechanism connected to the cuff through the valve could also be a vacuum device to provide for rapid depressurization of the cuff. In the preferred embodiment of the invention, the pressure release mechanism comprises a differential pressure sensor which compares the cuff pressure, with a reference pressure. The differential pressure sensor provides for release of fluid from the cuff until the cuff pressure is equal to the reference pressure. By varying the reference pressure, the pressure in the cuff during the exhalation mode of the respirator may be controlled.

The apparatus of the present invention also provides for adjustment of the pressure in the cuff during the inhalation mode and during the exhalation mode of the respirator. In order to adjust the pressure in the cuff during the inhalation mode of the respirator, the source of fluid presented through the valve to the cuff is regulated by a pressure regulator. A cuff pressure gauge is inserted in the line between the cuff and the valve so that as the high (systolic) pressure regulator is adjusted, the maximum pressure attained in the cuff can be determined. In order to vary the pressure of the cuff during the exhalation mode of the respirator, fluid under pressure is directed to the differential pressure sensor through a second pressure regulator which regulates the diastolic pressure in the cuff, that is, the lower limit of cuff pressure attained during the exhalation mode of the respirator. By adjusting the diastolic pressure regulator, the reference pressure at the differential pressure sensor may be varied and the amount of pressure released from the cuff will vary to correspond to this reference pressure. If one desires to maintain the pressure in the cuff at the high (systolic) pressure during the exhalation mode, the reference pressure presented to the differential pressure sensor would be the high (systolic) pressure of the inhalation mode.

The control mechanism for switching the valve between cuff-filling and cuff-emptying modes is preferably a pneumatic system wherein a control line is connected to one end to the exhalation valve supply pressure of the respirator and at the other end to the control apparatus. The pressure in the control line during the inhalation mode of the respirator is the pressure of the air used to actuate the exhalation valve of the patient manifold which permits respiratory air to be delivered to the airway and the tracheal tube. During the exhalation mode of the respirator, the control line is vented to atmospheric pressure. The exhalation valve pilot pressure is, in general, insufficient to actuate a conventional pneumatic valve. Therefore, the pressure received by the control apparatus from the exhalation valve supply is amplified by a conventional pneumatic power amplifier which presents to the cuff-filling and emptying valve a fluid having a sufficiently high pressure to actuate it. During the inhalation mode of the respirator, the fluid causes movement of valve member to switch the valve from the normally cuff-emptying mode to the cuff-filling mode to thereby pressurize the cuff. In the exhalation mode of the respirator, the valve is returned to the cuff-emptying state to provide for release of pressure within the cuff. It should be understood that the control mechanism for the cuff-filling and emptying valve is preferably a control system consisting essentially of pneumatic circuitry. However, it is envisioned that electrical control circuitry for operating the valve in accordance with the cycling of the respirator could be used.

It should be understood that the control apparatus of the present invention may be used with various types of cuffs. The most typical cuff has a defined volume which does not vary substantially when the cuff is pressurized. Another type of cuff is made of an elastic membrane and whose volume varies during pressurization and depressurization of the cuff. A third type of cuff, the cuff being known in the art as a "foam cuff", includes either a constant volume balloon or a variable volume balloon having a foam material disposes therein. The foam cuff is deflated, that is, a vacuum is applied to the balloon, in order to reduce the volume of the cuff during intubation. When the cuff is positioned within the trachea air is allowed to enter the interior of the balloon and the foam expands the cuff. The above-described three types of cuffs have features which allow them to be used with the apparatus of the present invention. During the inhalation mode of the respirator, the pressure in the cuff is greater than the pressure within the cuff during the exhalation mode of the respirator. These features are readily apparent with cuffs of the types having either a constant volume or a variable volume. However, the foam cuff, also has this feature in that the pressure within the cuff during the inhalation mode of the respirator is preferably approximately at atmospheric pressure while the pressure within the cuff during the exhalation mode of the respirator is preferably below atmospheric pressure. Thus, the control apparatus of the present invention provides for the pressure within the cuff to be higher during the inhalation mode of the respirator than during the exhalation mode of the respirator.

The apparatus of the present invention includes safety mechanisms which provide for inflation of the cuff should the supply of fluid under pressure to the control apparatus be temporarily cut off. Moreover, the control apparatus includes a safety mechanism whereby an alarm is sounded if the signal from the respirator to the control apparatus is terminated. The apparatus may also include a breath counter which counts the number of cycles of the respirator.

BRIEF DESCRIPTION OF THE DRAWING

The present invention may be better understood and its numerous objects and advantages will become apparent to those skilled in the art by reference to the accompanying drawing wherein like reference numerals refer to like elements in the several figures and in which:

FIGS. 3a and 3b are graphs showing the pressure in the airway of a respirator as a function of time and the pressure in the cuff as a function of time; and FIG. 4 is a schematic diagram relating to application of the present invention to a foam type cuff.

DETAILED DESCRIPTION OF THE INVENTION

Figure 1:
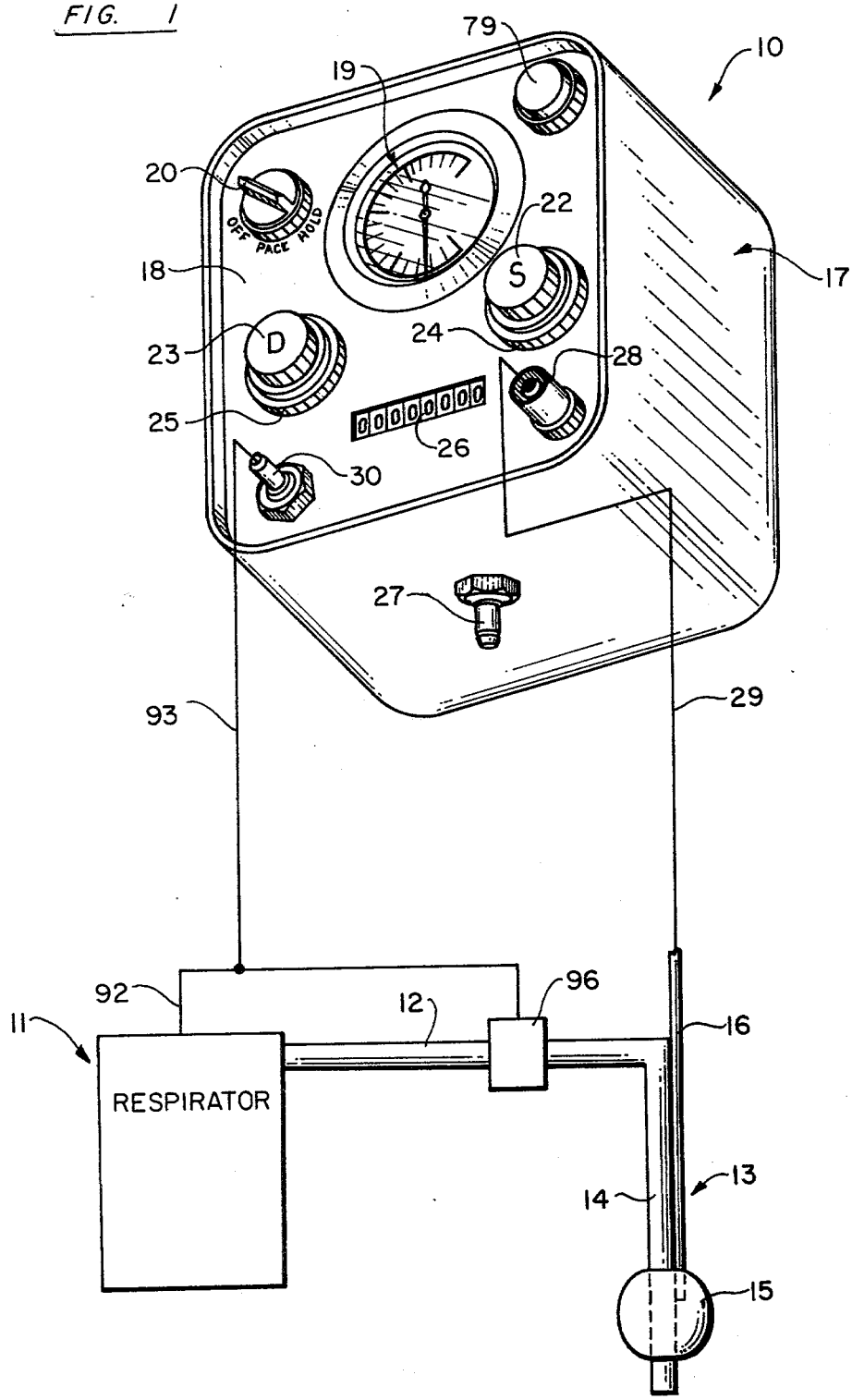
FIG. 1 is a perspective view of the apparatus for controlling the pressure in an endotracheal cuff.

Referring to FIG. 1, the apparatus 10 for controlling the pressure in a tracheal cuff is particularly suited for use with a conventional respirator 11 which is shown schematically. The respirator is of the type which cycles between an inhalation mode and an exhalation mode. During the inhalation mode, air or other gas is delivered through airway 12 to a tracheal tube 13 which is inserted in the trachea of a patient. The tracheal tube includes a passageway 14 for delivering air to the lungs of the patient. In order to seal passageway 14 with respect to the trachea, a pressure responsive tracheal cuff 15 is used. Cuff 15 may be pressurized and depressurized by air or other fluid introduced to and withdrawn from cuff 15 through conduit 16. It should be understood that the respirator and tracheal tube are shown schematically and are not part of the apparatus of the present invention. It should be understood that the control apparatus 10 may be used with various types of respirators, and, more particularly, with various types of tracheal tubes having pressure responsive cuffs.

The control apparatus 10 comprises a casing 17 and a front panel 18. The control apparatus 10 is particularly suited to be used with conventional respirators. However, it should be understood that the control apparatus 10 could be incorporated as an integral part of a respirator. A pressure gauge 19 is mounted on front panel 18 and indicates the pressure within the cuff 15. Control switch 20 provides for the selection of at least three modes of operation of pressure control apparatus 10. The switch can be placed in the "off" position wherein no fluid is delivered by control apparatus 10 to the cuff 15. The switch can be placed in a "pace" position wherein the pressure within cuff 15 is varied between a high or systolic pressure during the inhalation mode of the respirator and a low or diastolic pressure during the exhalation mode of the respirator. The switch 20 may also be positioned in the "hold" position wherein the pressure within the cuff 15 is maintained at the systolic pressure. Systolic pressure regulator 22 provides for adjustment of the cuff pressure during the inhalation mode of the respirator. Diastolic pressure regulator 23 provides for adjustment of the cuff pressure during the exhalation mode of the respirator. The controls for pressure regulators 22 and 23 include respective lock rings 24 and 25 which may be pushed in to lock the regulators at desired settings. When the tracheal tube 14 is inserted into the trachea of the patient, the pressure within cuff 15 during the inhalation and the exhalation mode of the respirator may be selected by turning systolic regulator 22 and diastolic regulator 23 and observing the pressure indicated on pressure gauge 19. Apparatus 10 further includes a breath counter 26 which reads and displays the number of cycles which the respirator has undergone. The breath counter 26 is resettable. The bottom of apparatus 10 includes an inlet port 27 to which a source of compressed fluid, such as compressed air or oxygen, is connected. The source may be from a tank of compressed air or oxygen or may be connected to wall compressed air or oxygen supply lines available in many hospitals. The pressure delivered to inlet 27 is preferably 50 psi.

Respirator signal inlet port 30 is connected via sensor conduit 93 to a T joint in exhalation valve supply 92 which delivers air to the exhalation valve of patient manifold 96. The conduit 16 leading to cuff 15 is connected to the cuff outlet 28 of apparatus 10 through which fluid is supplied to cuff 15. An alarm shut-off button 79 may be pressed to terminate the sounding of an alarm which indicates that the control apparatus 10 is no longer receiving input signals via sensor conduit 93.

Figure 2:
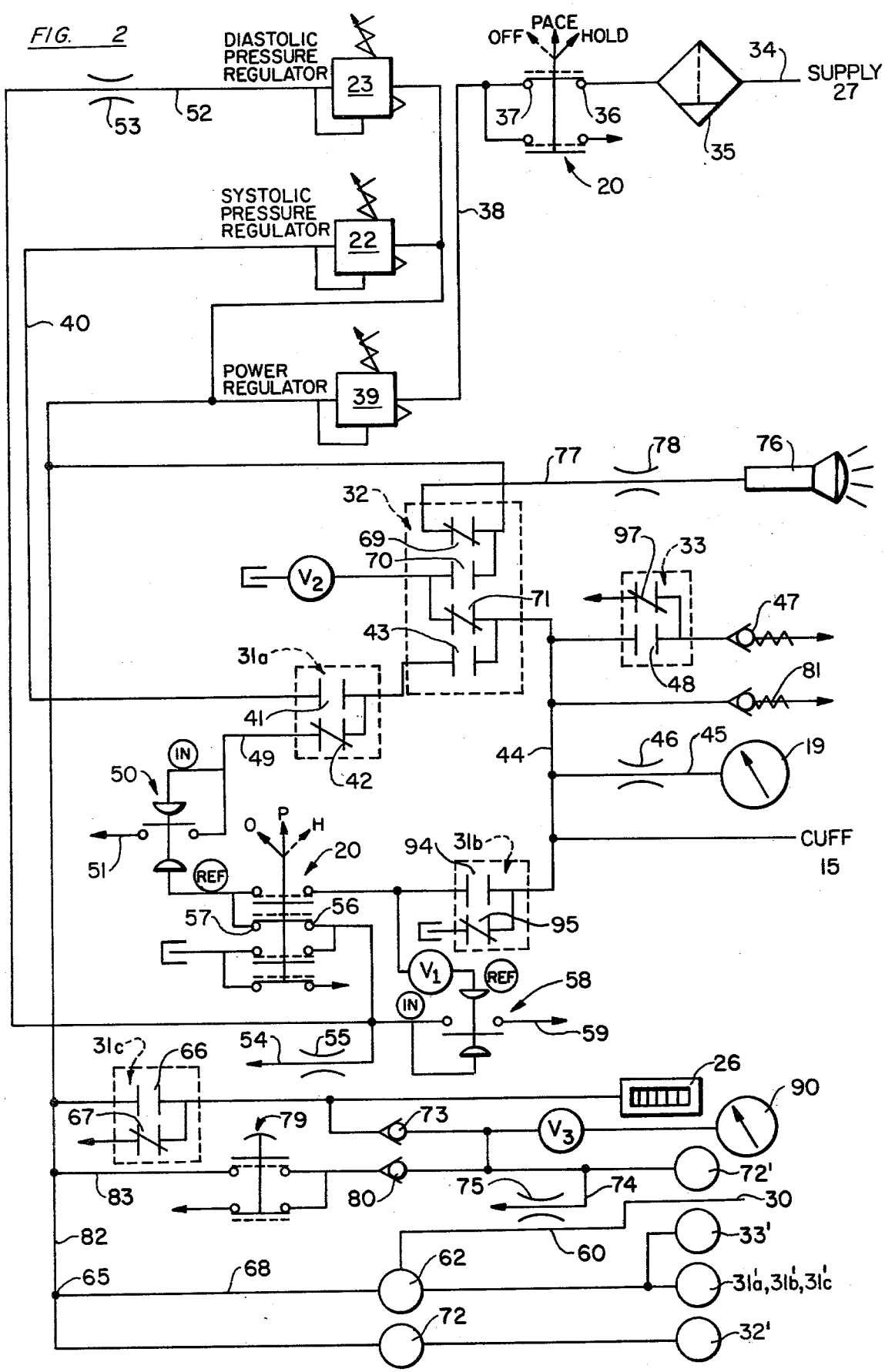
FIG. 2 is a pneumatic circuit diagram of the apparatus.

The manner by which the apparatus for controlling the pressure in the cuff functions will be apparent from the following description of the internal pneumatic circuitry of the apparatus. Referring to FIG. 2, the pneumatic circuitry of control apparatus 10 is shown. The symbols used to describe the components of the pneumatic circuitry are standard "Ladder Diagram" symbols well known in the art of pneumatic circuitry.

Valves 31a, 31b, 31c and 33 are three-port valves having two fluid passageways. Valve 32 is a five-port valve having four fluid passageways. The fluid passageways may be either in a passing or a not passing mode. A passing mode is indicated by a slash between two vertical lines. The not passing mode is indicated by the absence of the slash. Valves 31-33 function in a manner similar to an "OR gate". It should be understood, however, that each of the passageways in the "OR gate" valves functions as a valve, that is, the passageways may be placed in the passing mode to allow passage of fluid or placed in the not passing mode to prevent passage of fluid. Thus, any of the "OR gate" valves may be replaced by simple two-port valves which are operable between a passing and not passing mode.

Fluid under pressure is delivered through supply port 27. The pressure in the fluid should be in excess of 50 psi and the fluid can be, for example, compressed air or compressed oxygen. The source of the compressed air may either be a tank of compressed fluid or compressed fluid supply lines which are typically available in hospitals. The diagram will be described using compressed air. The compressed air enters through inlet 27 and is delivered to line 34. Line 34 directs the fluid through a fluid filter 35 which removes material which may tend to clog the components downstream of filter 35. The fluid is presented at port 36 of switch 20. When the switch is in the off position, the compressed air is prevented from passing downstream of switch 20. When switch 20 is in either the pace or the hold position, compressed air is allowed to pass from port 36 to port 37 and is presented to power regulator 39. Diastolic pressure regulator 23 and systolic pressure regulator 22 receive their pressure regulated air supply from the output at power regulator 39. As mentioned earlier, diastolic pressure regulator 23 may be used to control the pressure in cuff 15 during the exhalation mode of the respirator. Systolic pressure regulator 22 can be used to control the pressure in cuff 15 during the inhalation mode of the regulator. Power regulator 39 provides for pressure control of the supply of compressed air downstream of regulator 39. Normally, power regulator 39 is at a predetermined position with its adjusting knob locked in place and is not used by hospital personnel controlling the apparatus 10.

The manner in which the cuff is pressurized during the inhalation mode of the respirator will now be described. Compressed air is delivered through systolic pressure regulator 22 via line 40 to valve 31a. Valve 31a includes a first passageway 41 and a second passageway 42. Passageway 41 is normally in the not passing mode while passageway 42 is normally in the passing mode. Line 40 is connected to cuff 15 via valve 32, valve 32 being part of the safety circuit. As will be described hereinafter, when the apparatus 10 is switched to the pace or hold position, valve 32 will move from the normal position shown in FIG. 2 to a position wherein fluid will pass through passageway 43 into cuff 15.

When the respirator begins circulating air to the patient during the inhalation mode of the respirator, passageway 41 is moved to the passing mode by a control mechanism which will be described hereinafter. When passageway 41 is in the passing mode, cuff 15 is pressurized. It should be understood that the pressure presented through line 40 to valve 31a is above the pressure to which cuff 15 will be inflated. Thus, when passageway 41 is in the passing mode, the cuff 15 rapidly and almost instantaneously pressurizes. The pressure in the cuff may be read from cuff pressure gauge 19 which is connected through line 45 through a restrictor 46 to manifold 44. To insure that the pressure in the cuff does not reach undesirably high pressures, a spring operated preset pressure relief valve 47 is set to release pressures above 40 cmH$_2$O. It should be understood that valve 33 operates simultaneously with valve 31a so that passageway 48 is in the passing mode when passageway 41 is in the passing mode. To reiterate, when the respirator moves to the inhalation mode, passageway 41 is put in a passing mode and cuff 15 is presented with an instantaneous burst of air. Thus, cuff 15 rapidly or instantaneously pressurizes. However, air is released through pressure release valve 47 to insure that cuff 15 is not overpressurized. In order to adjust the pressure in cuff 15 during the inhalation mode of the respirator, systolic pressure regulator 22 may be turned so that the pressure presented to valve 31a varies. Upon cycling of the respirator, a person operating apparatus 10 reads cuff pressure gauge 19 and turns systolic pressure regulator 22 until the desired pressure in cuff 15 is reached. It should be understood that the passageway 41 functions as a simple valve means and allows a burst or pulse of air to rapidly pressurize cuff 15.

The manner in which the pressure of cuff 15 is controlled during the exhalation mode of the respirator will now be described. When the regulator moves to an exhalation mode, a control mechanism, which will be described hereinafter, switches valve 31a back to the position shown in FIG. 2 wherein passageway 42 is in the passing mode. If the pressure in the cuff is to be reduced to atmospheric pressure, line 49 may simply vent to atmosphere. Also if it is deemed desirable to depressurize cuff 15 rapidly, a vacuum mechanism may be connected to line 49 so that when passageway 42 is in the passing mode, air is evacuated from cuff 15. However, in the embodiment shown in FIG. 2, the pressure in cuff 15 during the exhalation mode of the respirator will be between atmospheric pressure and the systolic pressure of cuff 15. This is provided for by a differential pressure sensor 50. Differential pressure sensor 50 compares the pressure of inlet air to a reference pressure. If the inlet air pressure is greater than the reference air pressure, the differential pressure sensor 50 vents excess air to atmosphere through vent 51. Thus, the pressure in the cuff during the exhalation mode of the respirator is determined by the value of the reference pressure applied to differential pressure sensor 50. The reference pressure is provided by air which flows through diastolic pressure regulator 23 through line 52 via restrictor 53 to switch 20. Line 52 is connected through a restrictor 55 and vented to atmosphere through vent 54. Restrictors 53 and 55, and vent 54 form a pneumatic circuit that results in a responsive reference pressure range of 0–60 cmH$_2$O, using a pressure regulator that has an output range of 0–10 psi. Compressed air is delivered via line 52 to switch 20 at port 56. When the switch is in the off or pace position, the passage between port 56 and port 57 passes air and the reference pressure would be that provided through diastolic pressure regulator 23. Thus, by adjusting diastolic pressure regulator 23 and reading pressure gauge 19, hospital personnel can set the diastolic pressure to a value between atmospheric pressure and the maximum pressure provided through systolic pressure regulator 22. The diastolic cuff pressure may be set at a pressure other than atmospheric pressure to (1) retain PEEP; (2) prevent aspiration in comatose or obtunded patients or to; (3) allow for tracheal perfusion to continue in either of cases (1) and (2).

One of the safety features of the apparatus 10 will now be described. It is possible to turn diastolic pressure regulator 23 to a position wherein it provides differential pressure sensor 50 with a reference pressure greater than the pressure of air provided by systolic pressure regulator 22. Thus, but for the override pressure sensor mechanism which will now be described, the function of the diastolic pressure regulator 23 and the systolic pressure regulator 22 could be reversed. During the inhalation mode of the respirator, valve 31b is in a position wherein it passes air through passageway 94 to differential pressure sensor 58 which functions in a manner similar to differential pressure sensor 50. The diastolic pressure line 52 is presented to the inlet of differential pressure sensor 58 so that if the diastolic pressure exceeds the systolic pressure, excess diastolic reference pressure will be vented to atmosphere through vent 59. Of course, if the diastolic pressure equals the systolic pressure, cuff 15 will remain pressurized at the systolic pressure. In order to avoid having hospital personnel having to match the pressures provided by pressure regulators 23 and 22 by turning the regulators, a "hold" mode for apparatus 10 is provided. When switch 20 is turned to the hold position, the reference pressure presented to differential pressure sensor 50 is equal to the maximum systolic pressure in cuff 15. The systolic pressure in cuff 15 is presented to differential pressure sensor 50 through switch 20 and through one of the passages in valve 31b. Thus, in the hold mode of the apparatus, the pressure within cuff 15 will remain approximately at systolic pressure.

The control mechanism for operating valves 31a, 31b and 31c, will now be described. It should be understood that these three valves are part of a single relay valve having nine ports and three independent three-way circuits. Thus, valves 31a, 31b and 31c all function simultaneously. It should also be noted that valve 33 also functions simultaneously with valves 31a, b and c. However, a relay valve having twelve ports and four independent three-way circuits is not presently available so a valve 33 separate from valves 31a, 31b and 31c is used.

As described by reference to FIG. 1, the exhalation valve supply of the respirator is connected via inlet 30 to the control apparatus 10. It should be noted that any source of pressure having a rapid pressure rise which can be coordinated with the onset of inhalation may be used as a signal to the apparatus. Besides the exhalation valve supply, this source could be a nebulizer supply, the airway pressure itself, or an internal source of pressure within the respirator. The preferred source is the exhalation valve supply, as described herein. Since the pressure produced by the respirator at the exhalation valve supply is not sufficient to operate valves 31a, 31b, 31c, and 33, the respirator signal must be amplified. The pressure in the respirator during inhalation is presented through inlet 30 via line 60 to power amplifier 62. Power amplifier 62 permits the low pressure signal from the respirator to provide air having a relatively high pressure to pilot ports 31a', 31b', 31c' and 33' of valves 31a, 31b and 31c and valve 33. The compressed air supply is connected to power amplifier 62 via power regulator 39 to line 68 to manifold 82. Power amplifier 62 is connected to manifold 82 at port 65. As shown in the diagram, valves 31a, 31b and 31c and valve 33 are in their normal position. When the respirator moves to the inhalation mode, pressure is presented to power amplifier 62 which in turn provides sufficient pressure to pilot ports 31a', 31b', 31c' and 33' which activate valves 31a, 31b and 31c and valve 33. When the pressure in the exhalation valve supply of the respirator is removed as the respirator moves to the exhalation mode, power amplifier 62 ceases to supply pressure to hold the valves 31a, 31b and 31c and 33 in an actuated position and the valves return to the normal position.

A power amplifier, as used in the present invention has the operational characteristics of a 3-way pneumatic valve with a very low pilot pressure requirement. Thus, a power amplifier can control pressures of 20-30 psi with pilot or signal pressures of only 8 cmH$_2$O.

Breath counter 26 counts the number of times the respirator moves from the inhalation mode to the exhalation mode. Pressure delivered through passageway 66 of valve 31c when the respirator is in the inhalation mode advances the digital readout of the breath counter. The breath counter 26 could be a simple spring loaded piston mechanism whereby a piston rod produces an advancement of the numbers when it is presented with a pressure. When the respirator moves to the exhalation mode, passageway 67 is in a passing mode and the air previously delivered to the breath counter is released to atmosphere.

The safety mechanism which provides for pressurization of the cuff when the power supply fails will now be described. During operation of the apparatus, valve 32 is in a position opposite to that shown in the diagram. Thus, when the apparatus is operating, passageway 69 of valve 32 is not passing and passageway 70 of valve 32 is passing. Likewise, during operation of the respirator, passage 71 of valve 32 is not passing and passageway 43 of valve 32 is passing. Thus, volume V$_2$ is filled with compressed air at a pressure of approximately 25 psi. If the air power supply fails during operation of the apparatus, valve 32 moves to the position shown in the drawings. Volume V$_2$ would then be in communication with cuff 15 and cuff 15 would be pressurized. Valve 32 is controlled by power amplifier 72. During the period when the power supply is on, valve 31c periodically moves to a position where passage 66 is in a passing mode and air is delivered through one way check valve 73 to fill volume chamber V$_3$, register a positive pressure on alarm pressure gauge 90 and present a sufficient signal to pilot port 72' of power amplifier 72 which actuates valve 32. However, it should be noted that volume V$_3$ is bled through line 74 via restrictor 75 to the atmosphere. It has been determined that it takes approximately 15 seconds for the pressure within volume chamber V$_3$ to be reduced to a point wherein the power amplifier 72 no longer actuates valve 32 and this valve returns to its normal position. Thus, when the power fails, in about 15 seconds, passageway 71 of valve 32 moves to a passing condition and the air in volume V$_2$ pressurizes cuff 15.

During operation of the respirator, the pneumatic line circuited into inlet 30 may not provide a signal. This failure to provide a signal may be for various reasons including, for example, the kinking of the line between the exhalation valve supply of the respirator and respirator signal inlet 30. If this were to happen, alarm horn 76 would sound in about 15 seconds because passageway 69 of valve 32 would move to the passing mode and compressed air would be delivered through line 77 via restrictor 78 to alarm horn 76. As stated above, valve 32 returns to its normal position, wherein passageway 69 is placed in a passing mode, when amplifier 72 fails to actuate valve 32. This failure of amplifier 72 to actuate valve 32 is a direct result of amplifier 62 failing to receive a sensor signal from the respirator. When a signal is not received by amplifier 62 it fails to actuate valve 31c which is returned to its normal position, as shown in FIG. 2. As mentioned above when valve 31C is placed in its normal position, passageway 66 is placed in its non-passing mode and the fluid within chamber V$_3$ is depleted. With the chamber V$_3$ depleted and no fluid passing through passageway 66, amplifier 72 is deactivated and does not actuate valve 32. In order to turn the alarm horn off, spring operated push button valve 79 would be pressed thus presenting compressed air through line 83 via manifold 64 and check valve 80 to power amplifier 72. Of course, if the respirator signal and the power should fail simultaneously, the cuff would be inflated by volume $V_2$. In order to insure that cuff pressure 15 never exceeds a preset pressure, the manifold 44 to which cuff 15 is connected is also connected to a spring operated presettable pressure relief valve 81. This valve is normally selected to release air when the pressure is manifold 44 exceeds 80 cmH$_2$O.

It should be noted that when the apparatus is initially turned on and passageway 69 of valve 32 is in the passing mode, the alarm horn 76 may sound for a short time until the first pressure signal is presented to inlet 30. Of course, the alarm may be turned off by pressing push button valve 79.

The period of increase in the cuff pressure is determined by the respiratory cycle of the respirator attached to the patient. When the respirator begins its preset inspiratory cycle, a pressure pulse from the exhalation valve supply of the respirator is delivered to the exhalation valve of the remote patient manifold to cause the exhalation valve to close. Simultaneously, the airway is opened to inspiratory air. The same pulse or a simultaneous pulse triggers the control apparatus and air is delivered to cuff 15 as described above. When the inspiratory phase of the respirator is over, the signal from the respirator to the exhalation valve ceases and the exhalation valve shifts back to its normally open position thereby allowing exhalation to occur. Simultaneously, the apparatus 10 allows the cuff pressure to decay. FIG. 3 shows graphs which compare the airway pressure and the cuff pressure as functions of time. From the graphs shown in FIG. 3, it is apparent that inflation of the cuff occurs almost simultaneously with the increase of pressure in the airway. Moreover, decay of the pressure within the cuff occurs simultaneously with the decay in the airway pressure. In general it is also noted that the cuff pressure during inhalation is greater than the airway pressure thus providing for complete sealing of the tracheal cuff with respect to the tracheal tube. Thus, the control apparatus 10 shown in FIGS. 1 and 2 provides for nearly instantaneous pressurization of the cuff when the airway pressure is increased.

It should also be understood that the cuff pressure control apparatus may be modified so as to be used with what is known in the art as "foam cuffs". A tracheal tube including such a cuff is described in U.S. Pat. No. 3,640,282. A foam cuff typically includes a foam material surrounded by a balloon. The balloon is evacuated prior to intubation and once positioned within the trachea, air is allowed to enter the cuff and the foam within the balloon expands to press against the tracheal tube. Once the foam cuff is in position, deflation of the cuff in order to remove the cuff from the trachea may be accomplished by evacuating the cuff with a conventional syringe. It should be understood that the apparatus shown in FIGS. 1 and 2 could be modified to function with a foam cuff. FIG. 4 shows a simplified schematic of such an apparatus. Valve 100 is a three-way valve of the type previously described and includes passage 101 and passage 102. Foam cuff 103 is connected via passage 101 to a mechanism for providing positive pressurization of the foam cuff 103 during inhalation. The mechanism for providing positive pressurization of foam cuff 103 could be, for example, a vent to atmospheric pressure or could be a systolic pressure system similar to that shown in FIGS. 1 and 2. Thus, during the inhalation mode of the respirator, passage 101 is in the passing condition, and the foam within foam cuff 103 is allowed to expand. During the exhalation mode of the respirator, foam cuff 103 is connected via passage 102 to a mechanism for evacuating the cuff. Thus, by reducing the pressure within the cuff below atmospheric pressure, foam cuff 103 would contract during exhalation.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. Apparatus for regulating the fluid pressure within a conventional tracheal cuff, so as to inflate or deflate the cuff, coupled to a conventional automatic respirator which has inhalation and exhalation cycles, the respirator having associated therewith a source of pressurized fluid, the respirator providing a rapid pressure increase which is coordinated with the onset of inhalation, the regulating apparatus comprising;

adjustable pressure regulator means, said regulator means adapted to be in communication with the source of pressurized fluid associated with the respirator, said regulator means controlling the pressure of the pressurized fluid, said regulator means also setting the desired fluid pressure for inflation of a tracheal cuff and the desired fluid pressure for cuff deflation;

gate means, said gate means having multiple fluid passageways which may be opened or closed, said gate means having multiple ports which receive and discharge pressurized fluid, said gate means being coupled to said pressure regulator means and including connector means for coupling said gate means to a tracheal cuff associated with a respirator whereby said gate means may place said adjustable pressure regulator means in communication with the cuff when the respirator is in the inhalation cycle;

gate control means, said gate control means including connector means whereby said gate means may be coupled to the respirator, said gate control means controlling the opening and closing of said passageways of said gate means in response to the cycling of the respirator, said gate control means being in communication with said adjustable pressure regulator means; and cuff deflator control means, said deflator control means being in communication with said adjustable pressure regulator means, said deflator control means including connector means whereby said deflator control means may be placed in communication with the cuff through an open passageway of said gate means when the respirator is in the exhalation cycle, said deflator control means thereby causing adjustment of the fluid pressure in the cuff from said inflating pressure to said deflating pressure and maintaining said deflating pressure when the respirator is in the exhalation cycle.

2. The apparatus of claim 1 wherein said adjustable pressure regulator means is comprised of:

adjustable power pressure means, said power pressure means adjusting and setting the fluid pressure, said power pressure means in communication with said gate control means;

adjustable inflating pressure means, said inflating pressure means in communication with said power pressure means, said inflating pressure means setting the desired fluid pressure for cuff inflation, said inflating pressure means in communication with the cuff through an open passageway of said gate means when the respirator is in the inhalation cycle; and adjustable deflating pressure means, said deflating pressure means in communication with said power pressure means, said deflating pressure means setting the desired fluid pressure for cuff deflation, said deflating pressure means in communication with said cuff deflator control means.

3. The apparatus of claim 2 wherein said cuff deflator control means is comprised of;

pressure differential sensor means, said sensor means in communication with the cuff through an open passageway of said gate means when the respirator is in the exhalation cycle, said sensor means in communication with said adjustable deflating pressure means, said sensor means comparing the pressure of the fluid within the cuff with the fluid from said adjustable deflating pressure means when the respirator is in the exhalation cycle, said sensor means adjusting the fluid pressure within the cuff to said desired fluid pressure and maintaining said desired fluid pressure during the exhalation cycle.

4. The apparatus of claim 3 wherein said cuff deflator control means is further comprised of:

switch means, said switch means controlling the flow of pressurized fluid from the source to said adjustable power pressure means, said switch means further controlling the flow of the fluid from said adjustable deflating pressure means to said pressure differential sensor means, said switch means maintaining the cuff at said desired inflating pressure by disconnecting said adjustable deflating pressure means from said pressure differential sensor means.

5. The apparatus of claim 3 wherein said pressure differential sensor means adjusts the fluid pressure to said deflating pressure by venting the fluid to the surrounding environment.

6. The apparatus of claim 4 wherein said cuff deflator control means is further comprised of:

deflating sensor means, said deflating sensor means storing some fluid at said inflating pressure from the cuff said inflating pressure means through an open passageway of gate means during the inhalation cycle, said deflating sensor means comparing the fluid at said inflating pressure with fluid at said deflating pressure from said adjustable deflating pressure means during the exhalation cycle, said deflating sensor means adjusting said deflating pressure if it exceeds said inflating pressure.

7. The apparatus of claim 6 wherein said deflating sensor means adjusts said deflating pressure by venting some fluid to the surrounding environment.

8. The apparatus of claim 6 further comprising;

gauge means, said gauge means registering the fluid pressure within the cuff during both the exhalation and inhalation cycles; and adjustable excess fluid means, said excess fluid means being positioned in between the cuff and said open passageway of said gate means that connects said inflating pressure means and the cuff during the inhalation cycle, said excess fluid means venting excess fluid if the fluid pressure exceeds a given pressure.

9. The apparatus of claim 8 wherein said adjustable excess pressure means is a one-way check valve that releases fluid into the surrounding environment.

10. The apparatus of claim 8 further comprising:

safety means, said safety means in communication with said adjustable power pressure means through an open passageway of said gate means during both cycles, said safety means receiving a constant flow of the pressurized fluid from said adjustable power pressure means while the source is supplying the fluid, said safety means storing a set volume of pressurized fluid from said adjustable power pressure means, said safety means venting excess fluid to the surrounding environment, said safety means put into communication with the cuff through an open passageway of said gate means when the source fails to supply fluid, said safety means discharging pressurized fluid to the cuff through an open passageway of said gate means when the source fails to supply a fluid.

11. The apparatus of claim 10 wherein said safety means is capable of storing the pressurized fluid at 25 pounds per square inch.

12. The apparatus of claim 10 further comprised of:

adjustable pressure release means, said adjustable pressure release means being positioned between the cuff and said open passageway of said gate means that connects said safety means to the cuff, said release means preventing the pressure of the fluid from exceeding a predetermined pressure, said release means venting excess fluid into the surrounding environment.

13. The apparatus of claim 12 wherein said release means is an adjustable one-way check valve.

14. The apparatus of claim 12 wherein said gate means comprises:

first valve means, said first valve means being provided with two passageways and three ports;

second valve means, said second valve means being provided with four passageways and five ports;

third valve means, said third valve means being provided with two passageways and three ports;

fourth valve means, said fourth valve means being provided with two passageways and three ports;

fifth valve means, said fifth valve means being provided with two passageways and three ports;

said first valve means receiving fluid from said adjustable power pressure means and discharging fluid during the inhalation cycle to said second valve means and discharging the fluid during the exhalation cycle to said pressure differential sensor means of said cuff deflator control means;

said second valve means receiving fluid from said first valve means and discharging fluid to the third valve means and to said adjustable pressure release means of the said safety means and to said gauge means and to the cuff and through said fourth valve means during the inhalation cycle of the respirator, said second valve means receiving fluid from said safety means and discharging the fluid to said adjustable pressure release means and to said gauge means and to the cuff when the source fails to provide fluid;

said third valve means receiving fluid from said second valve means and discharging the fluid to said adjustable excess fluid means during the inhalation cycle of the respirator;

said fourth valve means receiving fluid from said second valve means and discharging the fluid to said deflating sensor means and said switch means of said cuff deflating means during the inhalation cycle of the respirator; and said fifth valve means receiving fluid from said valve control means and discharging fluid to said valve control means.

15. The apparatus of claim 14 wherein:

said first, third and fourth valve means are three port valves having two fluid passageways.

16. The apparatus of claim 14 wherein said valve control means comprises:

first amplifier means, said first amplifier means receiving fluid from said adjustable power pressure means, said first amplifier means discharging fluid from said adjustable power pressure means to said first, third, fourth and fifth valve means, said first amplifier means discharging fluid only after receiving fluid from the source of the fluid having a rapid pressure increase, said first amplifier means receiving said fluid from the source of the fluid having a rapid pressure increase only during the inhalation cycle;

said fluid which is discharged from said first amplifier means to said first, third, fourth and fifth valve means opening said passageways of said first, third, fourth and fifth valve means for the inhalation cycle;

one way stop means, said stop means providing only one way fluid passage, said stop means receiving fluid from said power pressure means through an open passageway of said fifth valve means during the inhalation cycle;

storage means, said storage means in communication with said stop means, said storage means receiving fluid from said stop means during the inhalation cycle, said storage means storing a volume of fluid, said storage means slowly venting fluid to the surrounding environment; and second amplifier means, said second amplifier means receiving fluid from said adjustable power pressure means, said second amplifier means discharging said fluid from said adjustable power pressure means to said second valve means, said second amplifier means discharging said fluid to said second valve means only when receiving fluid from said storage means.

17. The apparatus of claim 16 wherein said first and second amplifier means have operational characteristics of a three-way pneumatic valve with a very low pilot pressure requirement.

18. The apparatus of claim 16 further comprising:

distress signal means, said distress signal means receiving fluid from said power pressure means through said second valve means when said second valve means fails to receive said fluid from said second amplifier means, said second amplifier means failing to discharge said fluid to said second valve means when said second amplifier means fails to receive fluid from said storage means, said storage means failing to discharge said fluid to said second amplifier means when said storage means fails to receive fluid from said power regulator means through said fifth valve means and said stop means because said first amplifier means fails to discharge fluid to said fifth valve means, said first amplifier means fails to discharge fluid to said fifth valve means when said first amplifier means fails to receive said fluid from the source of the fluid having a rapid pressure increase.

19. The apparatus of claim 18 wherein said distress signal means is further comprised of:

button means, said button means providing fluid to said second amplifier means from said adjustable power pressure means when said first amplifier means fails to receive fluid from the source of fluid having a rapid pressure increase.

20. The apparatus of claim 19 wherein said button means is a spring operated push button valve.

21. The apparatus of claim 1 further comprising;

safety means, said safety means in communication with said adjustable power pressure means through an open passageway of said gate means during both cycles, said safety means receiving a constant flow of the pressurized fluid from said adjustable power pressure means while the source is supplying the fluid, said safety means storing a set volume of pressurized fluid from said adjustable power pressure means, said safety means venting excess fluid to the surrounding environment, said safety means put into communication with the cuff through an open passageway of said gate means when the source fails to supply fluid, said safety means discharging pressurized fluid to the cuff through an open passageway of said gate means when the source fails to supply a fluid.

22. The apparatus of claim 21 wherein said safety means is capable of storing the pressurized fluid at 25 pounds per square inch.

23. The apparatus of claim 21 further comprised of:

adjustable pressure release means, said adjustable pressure release means being positioned between the cuff and said open passageway of said gate means that connects said safety means to the cuff, said release means preventing the pressure of the fluid from exceeding a predetermined pressure, said release means venting excess fluid into the surrounding environment.

24. The apparatus of claim 23 wherein said release means is an adjustable one-way check valve.

* * * * *